US00PP16910P2

(12) United States Plant Patent
Hofmann

(10) Patent No.: US PP16,910 P2
(45) Date of Patent: Aug. 1, 2006

(54) **NEW GUINEA *IMPATIENS* PLANT NAMED 'FISNICS MAGPINK'**

(50) Latin Name: *Impatiens hawkeri*
Varietal Denomination: Fisnics Magpink

(76) Inventor: Birgit Christa Hofmann, Gassenweg 29, 56170, Bendorf (DE)

( * ) Notice: Subject to any disclaimer, the term of this patent is extended or adjusted under 35 U.S.C. 154(b) by 13 days.

(21) Appl. No.: 11/141,559

(22) Filed: May 31, 2005

(51) Int. Cl.
*A01H 5/00* (2006.01)

(52) U.S. Cl. ..... Plt./318
(58) Field of Classification Search ..... Plt./318
See application file for complete search history.

*Primary Examiner*—Kent Bell
(74) *Attorney, Agent, or Firm*—C. A. Whealy

(57) ABSTRACT

A new and distinct cultivar of New Guinea *Impatiens* plant named 'Fisnics Magpink', characterized by its outwardly spreading and uniformly mounded plant habit; low growth habit; freely branching and freely flowering habit; medium green-colored foliage; relatively short petioles; large, rounded, light red purple-colored flowers with light pink-colored stripes and margins; and flowers that are positioned above or beyond the foliage.

1 Drawing Sheet

Botanical designation: *Impatiens hawkeri.*
Cultivar denomination: 'Fisnics Magpink'.

BACKGROUND OF THE INVENTION

The present Invention relates to a new and distinct cultivar of New Guinea *Impatiens* plant, botanically known as *Impatiens hawkeri*, and hereinafter referred to by the name 'Fisnics Magpink'.

The new *Impatiens* is a naturally-occurring branch mutation of a proprietary seedling selection of *Impatiens hawkeri* identified as code number K02-9331-2, not patented. The cultivar Fisnics Magpink was discovered and selected by the Inventor as a branch mutation on a single flowering plant within a population of plants of the parent selection in a controlled environment in Hillscheid, Germany in June, 2002.

Asexual reproduction of the new cultivar by terminal cuttings taken in Hillscheid, Germany since September, 2002, has shown that the unique features of this new *Impatiens* are stable and reproduced true to type in successive generations.

SUMMARY OF THE INVENTION

The following traits have been repeatedly observed and are determined to be the unique characteristics of 'Fisnics Magpink'. These characteristics in combination distinguish 'Fisnics Magpink' as a new and distinct *Impatiens* cultivar:

1. Outwardly spreading and uniformly mounded plant habit; low growth habit.
2. Freely branching and freely flowering habit.
3. Medium green-colored foliage with relatively short petioles.
4. Large, rounded, light red purple-colored flowers with light pink-colored stripes and margins.
5. Flowers that are positioned above or beyond the foliage.

Plants of the new *Impatiens* can be compared to plants of the parent selection. In side-by-side comparisons conducted by the Inventor in Hillscheid, Germany, plants of the new

*Impatiens* differed from plants of the parent selection primarily in flower coloration as plants of the parent selection had lighter red purple-colored flowers without white-colored stripes and margins.

Plants of the new *Impatiens* can also be compared to plants of the cultivar Fisnics Pink, disclosed in U.S. Plant Pat. No. 13,228. In side-by-side comparisons conducted by the Inventor in Hillscheid, Germany, plants of the new *Impatiens* differed from plants of the cultivar Fisnics Pink in the following characteristics:

1. Plants of the new *Impatiens* were broader than plants of the cultivar Fisnics Pink.
2. Leaves of plants of the new *Impatiens* were larger and had shorter petioles than leaves of plants of the cultivar Fisnics Pink.
3. Plants of the new *Impatiens* had larger flowers than plants of the cultivar Fisnics Pink.
4. Plants of the new *Impatiens* and the cultivar Fisnics Pink differed in flower coloration as plants of the cultivar Fisnics Pink had intense pink-colored flowers with a distinct red purple-colored eye.

Plants of the new *Impatiens* can also be compared to plants of the cultivar Fisnics Light Pink, disclosed in U.S. Plant Pat. No. 13,579. In side-by-side comparisons conducted by the Inventor in Hillscheid, Germany, plants of the new *Impatiens* differed from plants of the cultivar Fisnics Light Pink in the following characteristics:

1. Plants of the new *Impatiens* were somewhat broader than plants of the cultivar Fisnics Light Pink.
2. Upper surfaces of leaf petioles of plants of the new *Impatiens* were pink in color whereas upper surfaces of leaf petioles of plants of the cultivar Fisnics Light Pink were green in color.
3. Plants of the new *Impatiens* and the cultivar Fisnics Light Pink differed in flower coloration as plants of the cultivar Fisnics Light Pink had light pink-colored flowers with a distinct red purple-colored eye.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new *Impatiens*. The photograph comprises a side perspective view of a typical flowering plant of 'Fisnics Magpink' grown in a container.

DETAILED BOTANICAL DESCRIPTION

The cultivar Fisnics Magpink has not been observed under all possible environmental conditions. The phenotype may vary somewhat with variations in environment such as temperature and light intensity, without, however, any variance in genotype.

The aforementioned photograph, following observations and measurements describe plants grown during the later winter and spring in Hillscheid, Germany, under commercial production practice in a glass-covered greenhouse. Rooted young plants were planted in 12-cm containers and the aforementioned photograph and following observations and measurements were taken about three months later. During the production of the plants, day temperatures were about 16 to 20° C. and night temperatures were about 16° C. In the following description, color references are made to The Royal Horticultural Society Colour Chart, 2001 Edition, except where general terms of ordinary dictionary significance are used.

Botanical classification: *Impatiens hawkeri* cultivar Fisnics Magpink.

Parentage: Naturally-occurring branch mutation of a proprietary seedling selection of *Impatiens hawkeri* identified as code number K02-9331-2, not patented.

Propagation:

*Type cutting.*—Terminal tip cuttings.

*Time to initiate roots.*—Summer: About 10 days at 24° C. Winter: About 12 to 15 days at 21° C.

*Time to produce a rooted cutting.*—Summer: About 15 days at 24° C. Winter: About 18 to 20 days at 21° C.

*Root description.*—Fine, fibrous; 158D in color.

*Rooting habit.*—Freely branching.

Plant description:

*General appearance.*—Outwardly spreading and uniformly mounded plant growth habit; low growth habit; freely branching habit; bushy appearance; freely flowering. Moderately vigorous.

*Crop time.*—From a rooted cutting, about nine weeks are required to produce finished flowering plants in 12-cm containers.

*Plant height.*—About 11.8 cm.

*Plant diameter or spread.*—About 22.8 cm.

*Lateral branches.*—Quantity per plant: About 14. Length: About 8 cm. Diameter: About 5 mm. Internode length: About 1 to 2 cm. Texture: Smooth, glabrous. Color: 143C tinged with 181A.

*Foliage description.*—Arrangement: Primarily in whorls. Length: About 12.3 cm. Width: About 4.4 cm. Shape: Elliptic. Apex: Acuminate. Base: Acute. Margin: Serrulate with ciliation. Texture: Smooth, slightly rugose; glabrous. Color: Developing foliage, upper surface; 141B to 141C. Developing foliage, lower surface: 139C. Fully expanded foliage, upper surface: 137A. Fully expanded foliage, lower surface: 139C. Venation, upper surface: 143C. Venation, lower surface: 144D. Petiole: Length: Relatively short, about 1.2 cm. Diameter: About 3 mm. Texture, upper and lower surfaces: Smooth, glabrous. Color, upper surface: 51D. Color, lower surface: 144D.

Flower description:

*Flower type and flowering habit.*—Single, large, rounded, light red purple-colored flowers with light pink-colored stripes and margins. Freely and continuously flowering; usually about six to nine flowers and flower buds per lateral branch. Flowers positioned above or beyond the foliage; flowers typically face parallel to the leaf canopy. Petals not persistent; gynoecium persistent. Flowers not fragrant.

*Flower longevity.*—Flowers last about one week on the plant.

*Flowering season.*—Year-round under greenhouse conditions. Plants begin flowering about nine weeks after planting.

*Flower buds.*—Length: About 2.2 cm. Diameter: About 1.6 cm. Shape: Ovoid. Color: 67C.

*Flower length.*—About 7.8 cm.

*Flower width.*—About 7.5 cm.

*Flower depth.*—About 1.2 cm.

*Petals.*—Quantity: Five per flower, imbricate. Length: Banner petals: About 3.3 cm. Lateral and base petals: About 3.4 to 3.6 cm. Width: Banner petal: About 5.5 cm. Lateral petals: About 3.2 cm. Base petals: About 3.8 cm. Shape: Cordate. Apex: Moderately lobed; emarginate. Base: Attenuate. Margin: Entire. Aspect: Mostly flat. Texture, upper and lower surfaces: Smooth; satiny. Color: When opening, upper and lower surfaces: N66C. Fully opened, upper surface: N66C; longitudinal stripes and towards the margins, 75D; no distinct eye. Fully opened, lower surface: N66C; towards the margins, 75D.

*Spur.*—Quantity: One per flower. Length: About 7 cm. Diameter: At apex: About 0.5 mm. At flower: About 3 mm. Aspect: Curved. Texture: Smooth, glabrous. Color: 53D.

*Peduncles.*—Length: About 5.5 to 6 cm. Diameter: About 2 mm. Texture: Smooth, glabrous. Strength: Strong, flexible. Color: 146D tinged with 181D.

*Reproductive organs.*—Androecium: Stamen number: Five fused at anthers, hooded; filaments free. Anther length: About 6 mm. Anther shape: Obovate. Anther color: 58B. Pollen amount: Moderate. Pollen color: 8D. Gynoecium: Pistil quantity: One per flower. Pistil length: About 5 to 6 mm. Stigma color: Close to 150D. Style color: 150D. Ovary: Five-celled. Ovary color: 143A.

*Seed/fruit.*—Seed and fruit development has not been observed.

Disease/pest resistance: Plants of the new *Impatiens* have not been observed to be resistant to pathogens and pests common to *Impatiens*.

Low temperature tolerance: Plants of the new *Impatiens* have been observed to tolerate night temperatures of 5° C. with 10° C. day temperatures.

It is claimed:

1. A new and distinct cultivar of New Guinea *Impatiens* plant named 'Fisnics Magpink', as illustrated and described.

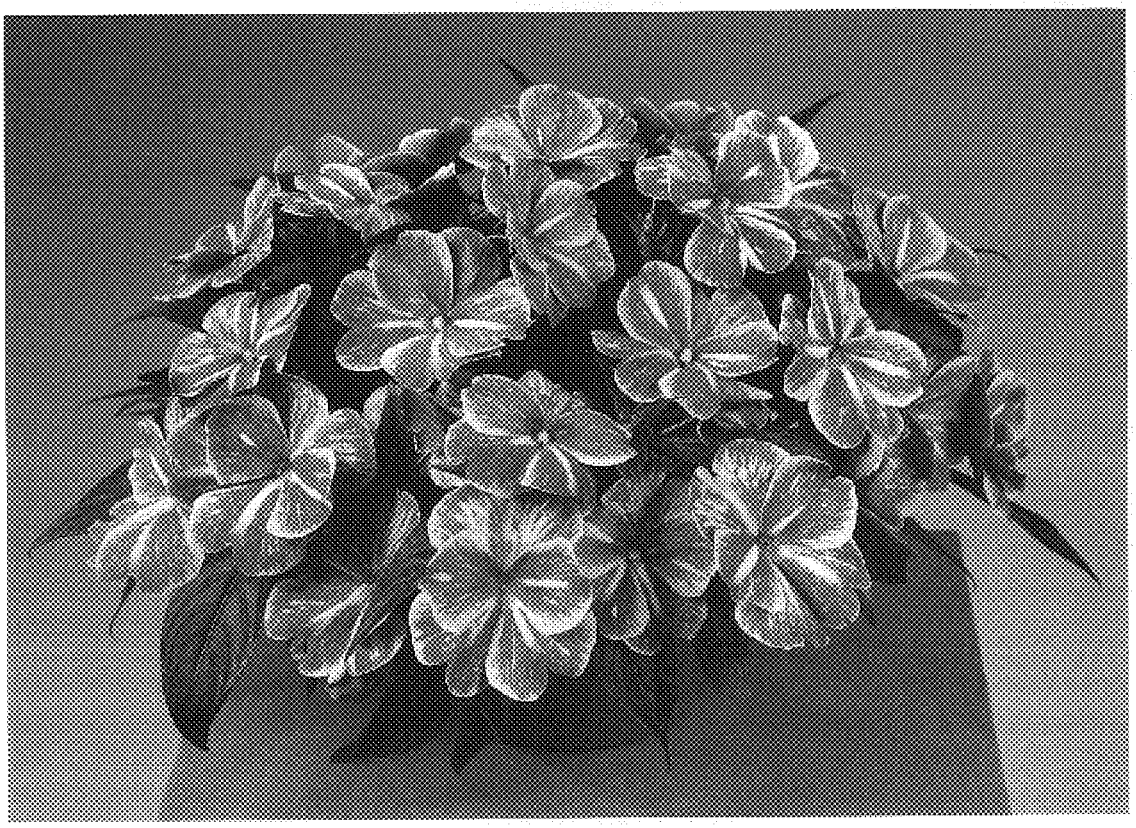

* * * * *